United States Patent [19]
Byrne, Jr.

[11] Patent Number: 5,770,116
[45] Date of Patent: Jun. 23, 1998

[54] GAME HUNTER'S SYSTEM AND KIT FOR TRACKING A WOUNDED ANIMAL AT NIGHT

[76] Inventor: Albert E. Byrne, Jr., 1323 Polo Run Dr., Yardley, Pa. 19067

[21] Appl. No.: 692,268

[22] Filed: Aug. 5, 1996

[51] Int. Cl.[6] .................................. C09K 3/00; F21K 2/00
[52] U.S. Cl. ............................................. 252/700; 362/34
[58] Field of Search ................................ 252/700; 362/34

[56] References Cited

U.S. PATENT DOCUMENTS

| | | | |
|---|---|---|---|
| 3,511,612 | 5/1970 | Kennerly et al. | 252/700 |
| 3,697,434 | 10/1972 | Shefler | 252/700 |
| 3,774,718 | 11/1973 | Morley | 252/700 |
| 3,893,938 | 7/1975 | Rauhut | 252/700 |
| 4,640,193 | 2/1987 | Koroscil | 362/34 |
| 4,706,568 | 11/1987 | Lundwall et al. | 362/34 |
| 5,001,880 | 3/1991 | Smith | 362/34 |
| 5,018,450 | 5/1991 | Smith | 362/34 |
| 5,338,494 | 8/1994 | Ritter et al. | 252/700 |
| 5,344,670 | 9/1994 | Palmer et al. | 362/34 |
| 5,381,311 | 1/1995 | Fujita | 362/34 |
| 5,430,662 | 7/1995 | Kuo | 362/34 |
| 5,552,968 | 9/1996 | Ladyjensky | 362/34 |

*Primary Examiner*—Philip Tucker
*Attorney, Agent, or Firm*—Cushman Darby & Cushman Intellectual Property Group of Pillsbury Madison & Sutro LLP

[57] ABSTRACT

A kit comprising (i) a chemiluminescent chemical capable of emitting visible light on contact with animal blood, (ii) a peroxy oxidizing agent contained in a disposable packet, (iii) an aqueous solvent which is free from components that would inhibit the functioning of component (i), (iv) a vessel suitable for mixing components (i), (ii) and (iii), and (v) a device for delivering the resulting mixture as a spray to an area of terrain suspected of having blood deposits thereon, whereby said spray upon contact with said blood will luminesce and emit visible light enabling recognition by the hunter of the presence of said blood and to assist in tracking and located said wounded game animal. Use of a luminol compound is preferred.

12 Claims, No Drawings

GAME HUNTER'S SYSTEM AND KIT FOR TRACKING A WOUNDED ANIMAL AT NIGHT

FIELD OF THE INVENTION

The invention relates to a system, kit and method for assisting game hunters in tracking and locating a wounded game animal at night or low light conditions, and in particular, a system, kit and method which makes use of a visible light-emitting composition having the capability of chemiluminescence when applied onto blood drops left by the wounded game animal.

DESCRIPTION OF RELATED ART

Dusk is one of the most active times for hunters of game animals. However, while hunting at dusk can be a productive strategy for hunters, it also poses a dilemma because tracking a wounded game animal with diminishing minimal light is very difficult. If a game animal is not killed instantly upon being shot by a hunter, the wounded game animal, acting with its heightened adrenaline flow, will immediately flee as rapidly as possible from the point at which it was wounded. Scattered blood drops from the wounded game animal, which during normal daylight hours would be useful in tracking the fleeing animal, are obscured at dusk or at night due to limited lighting. Furthermore, tracking is made difficult by, among other things, inconsistencies in the wounded game animal's blood flow and the varying textures and colors of the woodland floor. Therefore, traditional methods of tracking wounded game animals at dusk or in darkness are often futile, and a long felt need exists among game hunters to solve this problem. When such wounded animals are not located, the hunter's effort is wasted which results in both tangible economic and intangible psychological loss.

The object of the present invention, which makes use of chemiluminescent phenomena heretofore not applied to hunting, is to assist hunters in the tracking of game animals in the aforementioned minimal lighting conditions. Although chemiluminescent phenomena have long been known and used in various analytical arts, such arts are remote to the present invention. Chemiluminescent phenomena have not hitherto been exploited in endeavors for night tracking of wounded game animals.

SUMMARY OF THE INVENTION

These and other objects are met by the present invention which provides a method for enhancing the ability of a game hunter to track a wounded game animal under conditions of reduced visible light. The method comprises providing a kit comprising:

(i) a chemiluminescent chemical capable of emitting visible light on contact with animal blood,
(ii) a peroxy oxidizing agent contained in a disposable packet,
(iii) an aqueous solvent which is free from components that would inhibit the functioning of component (i),
(iv) a vessel suitable for mixing components (i), (ii) and (iii), and
(v) a device for delivering the resulting mixture as a spray to an area of terrain suspected of having blood deposits thereon; and spraying the area, whereby the spray upon contact with the blood will luminesce and emit visible light enabling recognition by the hunter of the presence of the blood and to assist in tracking and located the wounded game animal.

In addition, the invention provides a re-fill kit containing pre-packaged and pre-measured amounts of components (i), (ii), and (iii), as a concentrate for admixture to and with an additional pre-determined amount of aqueous solvent for refilling the vessel (iv).

The invention provides a convenient, costeffective method to avoid losing wounded game in the hunter's evening pursuits.

DETAILED DESCRIPTION OF THE PRESENT INVENTION

Tracking means the process of attempting to follow where an animal has gone. Tracking involves following not only the tracks of the animal in the soil, but also any other evidence left behind such as broken twigs and scattered blood. Night tracking means this process is done in conditions of low lighting found at dusk or after sun-down in substantial darkness. The use of an artificial light source, such as a flashlight, is generally ineffective under these conditions because it alerts the game animal to the hunter's location and distance, or due to difficult local terrain and foliage.

Visible light emitting chemical means a composition which emits light, as by chemiluminescence, of sufficient visibility such that a person attempting to track the wounded animal at night can perceive light emitting from mixture of scattered blood and the light emitting composition. A light emitting composition may in some cases emit some light without contact with blood. However, as known in the art, blood will otherwise catalyze and intensify the light emission so that a practical, useful visible selectivity is possible between that composition which is, and that which is not, mixed with blood. Night glasses, for example, may also be used to enhance the detection of the light emitting compositions.

The light-emitting composition is, in a preferred embodiment, prepared from the following starting ingredients: (i) a chemiluminescent compound or chemical formulation which can be oxidized, (ii) an oxidizing agent, and (iii) a, preferably, aqueous solvent.

The choice of chemiluminescent compound is limited only by the requirement that it can be oxidized and will on contact with animal blood perform the functions described herein. Sufficient visible light must be emitted on such contact. Similarly, the oxidizing agent is not particularly limited provided it can assist to induce the chemiluminescent compound to emit useful amounts of visible light. Finally, the solvent is not particularly limited provided that it can provide a medium containing the light emitting components in soluble, sprayable form, and will allow the necessary reactions to occur and allow for the composition to be sprayed or dispersed onto sites having scattered blood.

A variety of chemiluminescent compounds are envisioned, and mixtures can be used. Chemiluminescent compounds have been disclosed in, for example, U.S. Pat. Nos. 3,567,586 and 3,564,588, the complete disclosures of which are hereby incorporated by reference. Such compounds include, generally, cyclophthalhydrazides, among others. An exemplary natural chemiluminescent substance is luciferin, although synthetic substances are also known such as, for example, luminol or lucigenin. The chemiluminescent compound is preferably a cyclophthalhydrazide compound, and more preferably, a luminol compound. Chemiluminescent compounds of the cyclophthalhydrazide type have a useful peak emission from about 420–480 nm. Luminol itself, 3-aminophthalhydrazide, may be used.

Luminol can be obtained from, for example, Sigma Chemical Co. or Mallinckrodt, Inc. Other chemiluminescent substances are disclosed in, for example, U.S. Pat. No. 3,973,466, the complete disclosure of which is hereby incorporated by reference.

A variety of oxidizing compounds are envisioned, and mixtures can be used. The oxidizing compound can be, for example, a peroxy compound such as a perborate salt or hydrogen peroxide. Sodium perborate, $NaBO_3$, is convenient, and is presently preferred. However, other oxidizing agents such as, for example, cumene hydroperoxide, t-butyl hydroperoxide, succinic acid peroxide, hydroxyheptyl peroxide, sodium peroxicarbonate, and urea peroxide are contemplated. Substances such as sodium malate also could be added for purposes of stabilizing the chemiluminescent compound during storage.

The solvent, or solvent mixture, is preferably at least one inexpensive non-toxic polar solvent having the ability to dissolve sufficiently the aforementioned ingredients. Mixtures can be used. An aqueous solvent system is preferred, Solubility may be a function of pH. The preferred solvent is water, and more preferably, distilled water. The solvent should be free from contaminants which would interfere with the function of the chemiluminescent compound or the oxidizing agent.

These ingredients should be present in the amounts sufficient to be effective to facilitate the tracking purpose and such amounts can be readily ascertained by a person skilled in the art from the present disclosure with minimum experimentation. Preferred amounts range between about 0.2 g and about 5.0 g for the chemiluminescent compound, between about 1 g and about 10 g for the oxidizing agent, and between about 250 ml and about 1,000 ml of the solvent. These amounts, however, are not critical but are exemplary and are subject to optimization.

In the presently preferred embodiment, compositional ingredients are mixed just prior to use to form a solution which is distributed or sprayed by a hunter as, for example, a fine mist over an area where the hunter suspects that the game animal's blood may have been spilled. When the solution comes in contact with a trace of the game animal's blood, a chemical reaction known as chemiluminescence occurs. This reaction results in the emission of a (typically) bluish-white, or so-called cold light, from the blooded area which is visible even under poor lighting conditions. By repeating the solution spraying process in the direction of the game animal's flight, and thus repeating the luminescent reaction initiated by the contact of the composition and the game animal's blood, it is possible to create a luminescent trail by which the hunter can track the wounded game animal until found.

The distribution means, methods, and devices are not particularly limited provided that the kit is practical and operable for hunters. The means, methods, and devices, for example, should allow the kit to be portable. Conventional hand-operated spray or pump heads, known to those skilled in the art, can be used, or alternatively, for example, an aspirator head or air-pressure assisted devices. Spraying luminescent aerosols is disclosed in, for example, U.S. Pat. No. 3,744,718, the complete disclosure of which is hereby incorporated by reference. As an example of the practice of this invention, the chemical formulation which creates the luminescent effect when it comes in contact with animal blood can be formulated by mixing in about 500 ml of distilled water about 0.5 g of dry luminol (3-aminophthalhydrazide) with about 25 g of dry sodium carbonate as a buffer. Just prior to use, a mixture of about 3.5 g of dry sodium perborate oxidizing agent is added thereto. These separate components can also be pre-prepared in respective solutions and then those solutions combined in the amounts indicated.

The light emitting reaction is a chemiluminescent reaction based upon the oxidation of, for example, luminol in an alkaline solution in the presence of an oxidizing agent such as, for example, sodium perborate, and a peroxidase system as found within the hemoglobin molecule of blood. The drying blood exposes the heme molecule to allow it to catalyze the reduction of peroxy compounds like sodium perborate through its peroxidase-like activity. This in turn catalyzes the oxidation of luminol by mechanisms known in the art. The present invention, however, is not limited by the theory and nature of such mechanisms. Other luminescent mechanisms may be employed.

Alkaline conditions are preferred for the chemiluminescent reaction to occur, and in particular, pH of between about 8.5 and about 11 is preferred. For example, the aforementioned luminol reaction in the presence of sodium carbonate, $Na_2CO_3$, creates an optimal alkaline solution of pH about 9–11, preferably, 10.4–10.8 with sodium perborate as an oxidizing agent, luminol as the substance to be oxidized, and with distilled water as solvent. Bicarbonate substances are also envisioned to help control pH. For instance, sodium bicarbonate may also be used. Other pH's, however, may be used provided that the advantages of the present invention can be achieved.

For maximum efficiency, the composition ingredients are preferably added in any particular order to the solvent such as distilled water. The person skilled in the art will be able to experiment with the order of mixing to obtain optimal results. Some ingredients, for example, may be premixed before mixing all ingredients together.

In a preferred embodiment, sodium perborate is more soluble in water than sodium carbonate, while luminol is more soluble in water containing sodium carbonate. Therefore, the following exemplary formulation strategy or recipe can be used.

ACTIVE INGREDIENTS

I. 3.5 g sodium perborate

II. 0.5 g luminol+25.0 g sodium carbonate

III. 500 mL distilled water

Ingredients I and III are mixed and shaken well. Ingredient II is added to the solution and shaken well. Preferably, the solution should be made up just prior to use to retain its full potency and sensitivity. The solution is typically most effectively used within about eight hours of mixing, depending upon ambient temperatures (higher temperatures may lead to an abbreviated active lifetime of the mixture).

At the moment the shot and hit occurs, and assuming that an instantaneous kill is not achieved by that shot, the hunter should note both the exact location of the game animal at the time of impact, and the direction of flight from the impact area. As soon as realistically possible, the point of impact should be confirmed by observing the terrain for signs of spilled blood, tissue, or other evidence of impact. This point will act as the point of origin from which the tracking process can begin.

The product of this invention can be used by the hunter at any point, or points, in the tracking process upon the loss of sufficient natural light including the establishment of the origination point and blood trail. Following the shot, the hunter can wait approximately 15–30 minutes before beginning the tracking of the wounded animal. From the point of impact, the hunter should proceed along the suspected line of the wounded game's flight searching for further evidence of the impact such as a blood trail. If sufficient light is available, the blood trail should be marked by the hunter with an easily identifiable item so that a more permanent trail may be established to aid in tracking.

The hunter can practice the present invention with use of a portable kit. The kit should be so designed as to permit easy assembly and use and appropriate size, along with ease of portability. Portability means that the hunter and those skilled in the art can effectively carry and use the kit. The precise conditions under which hunters operate vary, and the kit can be modified accordingly to serve practical needs. This is well within the skill of the art.

In one embodiment of this invention, and at the point where natural light is no longer sufficient to track the wounded game, the hunter would open a container, for instance a packet, containing, for example, the sodium perborate and thoroughly combine this with the distilled water, or other suitable solvent, in a vessel to which a spray head can be attached. After this solution is mixed well, a separate container or packet containing, for example, the luminol and sodium carbonate mixture should be added to the solution which is then shaken to effect adequate dissolution. Once prepared, the chemical solution of the kit can be sprayed in a fine mist in the suspected area or direction of the game's flight. When the kit's luminescent agent comes in contact with animal blood, chemiluminescence occurs as already described.

The kit should be of such effective design and size to allow for the tracking to begin within about 30 minutes, and preferably within about 10–15 minutes, from when the game animal is first wounded.

In a preferred embodiment, the kit contains a spraying device containing the appropriate amount of aqueous dissolving medium. Two containers or packets may be provided in the form of, for example, foil, plastic, or paper. One container or packet will contain the sodium perborate in a dry powder form, or as, for example, a compressed tablets. The second container will contain a mixture of luminol and sodium carbonate in a dry powder form, or as, for example, a compressed tablet or tablets. The respective packets or tablets will contain a pre-measured or dosed amount of the ingredients for mixing in the pre-determined volume of aqueous solvent.

When the components are prepared in tablet form, the usual, well-known, tableting aids may be incorporated to form the tablet, such as binding agents, tablet disintegrating agents to aid break up of the tablet, and release agents which facilitate the release of the tablet from the tablet-forming machinery. Of course, the just-mentioned ingredients should be substantially inert to the packaged active ingredients of this invention. Preferably, even in tablet form, the ingredients are pre-packaged in substantially water-impervious disposable containers, such as foil or plastic mini-envelopes or alternatively tubular dispensing containers. By this means a substantial, indefinite shelf-life of the active ingredients can be achieved.

The kit can also be designed to allow for replacement packages or containers. This means that after the kit is used, it need not be totally replaced. Rather, secondary kits can be purchased containing, for example, the aforementioned packets or compressed tablets of ingredients. Hence, compositions can be prepared comprising a mixture of the following ingredients before mixing: (i) a luminol compound, and (ii) an alkaline base ingredient. Varying fill sizes and accessories can be employed by the person skilled in the art to practice the present invention.

A pre-mixed composition or concentrate can be added which contains, for example, pre-measured amounts of solubilizers such as methyl or ethyl alcohol which may aid dissolution of the organic component. In addition, one or more surface active agents may be added to improve performance. For instance, non-ionic, cationic or anionic surface active agents or detergents may be suitably employed. By reducing the surface tension of the water, these latter agents may aid in spreading the applied spray on the terrain to assist it in reaching contact with blood deposits. Colorants may also be added, if desired, provided that they do not interfere with the light emitting characteristics of the chemiluminescent component.

While the invention has been described in detail and with reference to specific embodiments thereof, it will be apparent to those of ordinary skill in the art that various changes and modifications can be made therein without departing from the spirit and scope thereof.

What is claimed is:

1. A kit comprising:

(i) a first container for and containing a pre-measured amount of a chemiluminescent chemical capable of emitting visible light on contact with animal blood, (ii) a second container for and containing a pre-measured amount of a peroxy oxidizing agent, (iii) an amount of aqueous solvent for said pre-measured amounts of (i) and (ii) which is free from contaminants that would inhibit the functioning of component (i), (iv) a vessel suitable for mixing components (i), (ii) and (iii), and (v) a device suitable for delivering the resulting mixture or solution as a spray from said vessel to an area of terrain suspected of having blood deposits thereon, whereby said spray upon contact with said blood will luminesce and emit visible light enabling recognition by a hunter of the presence of said blood and to assist in tracking and locating a wounded game animal.

2. A kit according to claim 1, wherein said chemiluminescent chemical is a cyclophthalhydrazide compound.

3. A kit according to claim 1, wherein said chemiluminescent chemical is a luminol compound.

4. A kit according to claim 1, wherein said chemiluminescent chemical is luminol.

5. A kit according to claim 1, wherein said peroxy oxidizing agent is a borate salt.

6. A kit according to claim 1, wherein said solvent is distilled water.

7. A kit according to claim 1, wherein said aqueous solvent also contains a water miscible alcohol in sufficient quantity to aid dissolution of the chemiluminescent component and a surface active agent for aid in dispersing the solution upon spraying.

8. A kit according to claim 1, wherein said solvent is distilled water, said peroxy oxidizing agent is a borate salt, and said chemiluminescent chemical is a cyclophthalhydrazide compound.

9. A kit according to claim 1, wherein said mixture is at alkaline pH after mixing of said components.

10. A kit according to claim 9, wherein said alkaline pH is generated by use of a carbonate salt.

11. A refill kit for the combination of claim 1 containing (i) a first container for and containing a pre-measured amount of chemiluminescent compound, (ii) second container for and containing a pre-measured amount of a peroxy oxidizing agent, and adapted for re-constituting a pre-determined amount of the combination of claim 10 upon addition thereof to the aqueous solution.

12. A refill kit according to claim 11 further including a concentrate composed of a pre-measured amount of a water-miscible alcohol and a surface active agent for addition to an aqueous medium to reconstitute said aqueous solvent.

* * * * *